United States Patent [19]

Altamura et al.

[11] Patent Number: 5,364,768
[45] Date of Patent: Nov. 15, 1994

[54] PROCESS FOR THE PREPARATION OF PENEMS

[75] Inventors: Maria Altamura; Franco Francalanci; Marcello Marchi, all of Novara, Italy

[73] Assignee: Farmitalia Carlo Erba S.r.l., Milan, Italy

[21] Appl. No.: 940,784

[22] Filed: Sep. 4, 1992

Related U.S. Application Data

[63] Continuation of Ser. No. 496,054, Mar. 16, 1990, abandoned, which is a continuation of Ser. No. 216,232, Jul. 7, 1988, abandoned.

Foreign Application Priority Data

[30]

Jul. 7, 1987 [GB] United Kingdom .............. 8715992

[51] Int. Cl.$^5$ ............................................. C12P 37/00
[52] U.S. Cl. ................................. 435/43; 435/197; 435/198
[58] Field of Search ............ 435/43, 118, 119, 197, 435/198, 135, 280

[56] References Cited

U.S. PATENT DOCUMENTS 5,215,891  3/1992  Altamura .................... 435/43

FOREIGN PATENT DOCUMENTS

| 2043639 | 10/1980 | United Kingdom | 435/43 |
| 2086897A | 5/1982 | United Kingdom . | |
| 2144743 | 8/1983 | United Kingdom | 435/43 |
| 2118181 | 10/1983 | United Kingdom | 435/43 |
| 2133010 | 7/1984 | United Kingdom | 435/43 |

*Primary Examiner*—Irene Marx
*Attorney, Agent, or Firm*—Oblon, Spivak, McClelland, Maier & Neustadt

[57] ABSTRACT

An in vitro process for preparing 6((1R)-hydroxyethyl) penem acids by hydrolyzing the carboxylic ester derivative thereof using an enzyme capable of selectively hydrolyzing the ester group at the 3-position of the carboxylic acid ester using an esterase, acylase or lipase enzyme, wherein the enzymatic hydrolysis is effected at a pH in the range of from 5 to 8 and at a temperature in the range of 20° C. to 40° C.

4 Claims, No Drawings

PROCESS FOR THE PREPARATION OF PENEMS

This is a continuation of application Ser. No. 07/496,054, filed Mar. 16, 1990, now abandoned, which is a continuation of Ser. No. 07/216,232, filed Jul. 7, 1988, now abandoned.

BACKGROUND OF THE INVENTION

FIELD OF THE INVENTION

Compounds of the formulas I and II are known as antibacterial agents as described in UK Patent Applications No. 2043639-A, 2097786-A, 2118181-A, 2133010-A, EP 0167100-A, EP 0166972-A, EP 0199446-A, EP 02011206-A and in European Patent Application No. 87 102825.4, filed on Feb, 27, 1987.

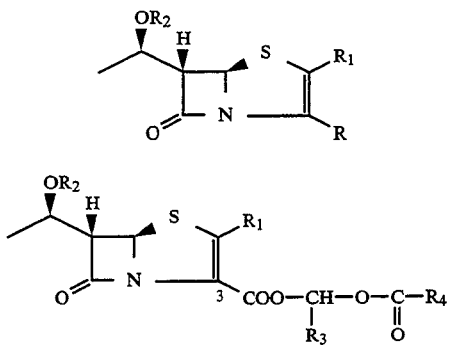

As described in the above cited patent applications and also in UK Patent Application No. 2144743 and in EP 0188247-A, compounds of formula I and II are prepared by different chemical syntheses. Alternatively, compounds of formula II can be prepared by esterification of compounds of formula I.

However, no practical method is presently available to transform compounds of formula II into compounds of formula I in good yield.

In order to avoid side reactions during the penem syntheses described in the above cited prior art, it is necessary to protect the 2-carboxy group. For this purpose, a group of formula $-CHR_3-OCO-R_4$ may be employed.

In the above formula $-CHR_3-OCO-R_4$, $R_3$ is a hydrogen atom or a $C_1-C_6$ alkyl group, and $R_4$ is a hydrogen atom or an alkyl, alkenyl, alkoxy, phenyl, phenylalkenyl or phenylalkyl group having from 1 to 18 carbon atoms.

Moreover, such compounds of formula II are useful as orally adsorbed esters, as described in UK 2133010-A.

A simple conversion of compounds of formula II into compounds of formula I would allow for the preparation in a few steps of both the useful "in vivo+ hydrolyzable esters and the corresponding acids.

Further, it would also be desirable to have a method for converting a stored amount of a stable oral antibiotic drug of formula II into the corresponding acid or salt thereof, which could be formulated as a useful parenteral drug.

However, at present, no method is known which satisfies the above conditions.

SUMMARY OF THE INVENTION

It is an object of the present invention to provide a process for the preparation of compounds of the formula I.

Moreover, it is also an object of this invention to provide such a process using a selective and inexpensive enzymatic hydrolysis of compounds having the formula II.

DETAILED DESCRIPTION OF THE PREFERRED EMBODIMENT

The present invention relates to a novel process for preparing 6-[(1R)-hydroxyethyl] penem acids having antibacterial activity.

More particularly the invention relates to a process for the preparation of compounds of formula I:

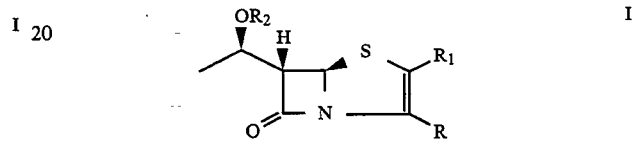

wherein R represents a carboxy group or a carboxylate anion; R1 is a tetrahydrofuranyl or an optionally substituted $C_1-C_4$ alkyl, methylphenyl or methylphenoxymethyl group, the substituents being:

(i) hydroxy, amino, carbamoyloxy, $C_1-C_{18}$ alkoxy or carboxy groups or a halogen atom, (ii) optionally substituted heterocyclylthio radical having up to 10 carbon atoms and up to 4 ring heteroatoms, selected from nitrogen, oxygen and sulfur, the substituents being as defined above under (i) or a $C_1-C_4$ alkyl, oxo, or carbamoyl group, (iii) an optionally substituted or fused pyridinium, N-methylpyrrolidinium or piperidinium group, the substituents being,as defined above under (i) or a $C_1-C_4$ alkyl group optionally substituted by sulfonyloxy or carboxy group, and $R_2$ represents a hydrogen atom or a hydroxy protecting group; by enzymatic hydrolysis of compounds of formula II:

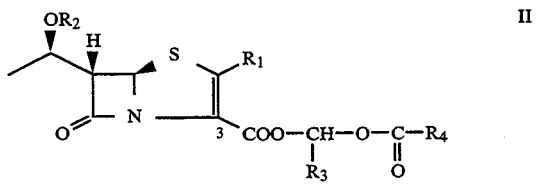

wherein $R_1$ and $R_2$ are as defined above, $R_3$ represents a hydrogen atom or an alkyl group having from 1 to 6 carbon atoms, and $R_4$ is a hydrogen atom, an alkyl, alkenyl, phenyl, phenylalkenyl or phenylalkyl group having from 1 to 18 carbon atoms or an alkoxy group.

The hydroxy protecting groups which $R_2$ may represent include p-nitrobenzyloxycarbonyl, 2,2,2-trichloroethoxycarbonyl, trimethylsilyl, benzyl, p-bromophenacyl, triphenylmethyl and pyranyl groups.

In a preferred aspect, the invention is directed to a process for the preparation of compounds of formula I, wherein R1 is carbamoyloxymethyl, methoxymethyl, pyridiniomethylphenyl, pyridiniomethylphenoxymethyl or carboxymethylpyridiniomethylphenyl group. Preferred protecting groups which $R_2$ may represent are p-nitrobenzyloxycarbonyl, trimethylsilyl and pyranyl groups.

The present invention provides a simple process for the preparation of compounds of formula I by selective and inexpensive enzymatic hydrolysis of compounds of formula II as defined above.

The process of the invention, using enzymatic hydrolysis, allows the final product to be obtained under very mild conditions, in very high yield and without undesired by-products.

The configuration of the compounds of formula II is [5R,6S,(1R)], in order to obtain the preferred final [5R,6S,(1R)] stereochemistry of the penem nucleus.

Immobilization or insolubilization is advantageous as the same enzyme can be used for many production cycles.

The use of the enzymes isolated and purified to the desired degree is preferred rather than the raw cellular extract since the extraction or purification process normally allows a reduction or elimination of the presence of contaminating enzymes which could lower the yield by formation of undesired by-products.

Also enzymatic preparations obtained by extraction of animal organs, such as porcine pancreas, liver or kidney, are able to cause hydrolysis of the ester bond.

Commercially available hydrolytic enzymes can be used in the enzymatic process, for example:

| Enzyme | Origin | Seller |
|---|---|---|
| PPL | Porcine pancreas | SIGMA Chem. Co. - St. Louis (USA) |
| Pancreatin | Porcine pancreas | UNIBIOS - Trecate (Italy) |
| Esterase | Porcine Liver | SIGMA Chem. Co. - St. Louis (USA) |
| Lipase | *Chromobacterium Viscosum* | TOYO JOZO (Japan) |
| Cholesterol esterase | Pseudomonas Sp. | TOYOBO (Japan) |
| Lipase B | *Penicillum Liliacinum* | FARMITALIA C. ERBA (Italy) |
| Lipase FAP 15 | *Rhizopus Javanicus* | AMANO (Japan) |
| Protease | *Aspergillus sojae* | SIGMA Chem. Co. - St. Louis (USA) |
| Lipase N conc. | *Rhizopus Niveus* | AMANO (Japan) |
| Lipase A 6 | *Aspergillus Niger* | AMANO (Japan) |
| Lipase | Wheat germ | SIGMA Chem. Co. - St. Louis (USA) |
| Lipase | *Rhizopus Delamar* | SIGMA Chem. Co. - St. Louis (USA) |
| Protease | Rhizopus Sp. | SIGMA Chem. Co. - St. Louis (USA) |
| Lipase P | Pseudomonas Sp. | AMANO (Japan) |
| Acylase I | Porcine kidney | SERVA (W. Germany) |
| Lipase SP 225 | | NOVO Industri (Denmark) |
| Papain | | SIGMA Chem. Co. - St. Louis (USA) |
| Lipoprotein Lipase | Pseudomonas Sp. | TOYOBO (Japan) |
| Protease | *Aspergillus Saitoi* | SIGMA Chem. Co. - St. Louis (USA) |
| Lipase OF | Candida Cylindracea | SANKYO (Japan) |
| Lipase CES | Pseudomonas Sp, | AMANO (Japan) |
| Lipase 6 | *Penicillum Cyclopium* | AMANO (Japan) |
| Lipase R-10 | *Penicillum Roqueforti* | AMANO (Japan) |
| Lipase L-10 | *Candida Lipolytica* | AMANO (Japan) |
| Lipase D-20 | *Rhizopus Delamar* | AMANO (Japan) |
| Lipase AY 30 | *Candida Cylindracea* | AMANO (Japan) |

For $R_3$ and $R_4$ of the compounds of formula II, alkyl is preferably methyl, ethyl, propyl, butyl; alkenyl is allyl, methylallyl; phenylalkenyl is styryl; phenylalkyl is phenylethyl, phenylpropyl, and alkoxy is methoxy or ethoxy.

Preferably, $R_3$ represents a hydrogen atom or a methyl group and $R_4$ represents a methyl, ethyl or methoxy group. Most preferably, $R_3$ is a hydrogen atom and $R_4$ represents a methyl group.

The starting materials of formula II can be conveniently prepared in 8 steps from 6-aminopenicillanic acid as described in EP 0188247-A.

The present invention, therefore, allows the direct synthesis of compounds of formula I directly from 6-aminopenicillanic acid, which is the most straightforward synthesis of the penem acids of formula I.

Hydrolytic enzymes suitable for use in the present process are, for example, lipases, esterases or proteases which selectively hydrolyze the carboxylic ester of compounds of formula II without affecting other functional groups which may be present.

The hydrolytic process can be carried out either by using directly the free or immobilized microbic cells or by isolating the specific enzymes which can be used in the free form, immobilized according to known techniques to resins, glass, cellulose or similar substances by ionic or covalent bonds, or grafted to fibres permeable to the substrate, or insolubilized by cross-linkage.

The enzymes may be added to an aqueous suspension of from 1 to 100 g/l of the ester of formula II, suitably mildly buffered at different pH according to the enzyme used, that is in a range from about 4 to 10, preferably from about 5 to 8.

The reaction may be carried out at a temperature of from about 10° C. to 50° C., preferably from about 20° C. to 40° C., for about 0.5 to 48 hours, operating in batch or column, according to the quantity of the enzyme present in the reaction mixture, and to the ratio between the quantity of the enzyme in solution or in the immobilized form, and the quantity of substrate present in the reaction mixture.

The pH of the reaction mixture is kept constant at the desired value by adding a solution of an alkali hydroxide.

The yields of the reaction carried out under optimal conditions reach values higher than 90%.

At the end of the reaction, the reaction product can be recovered by conventional methods.

The present invention will now be more fully described by means of the following examples, which are provided merely for purposes of illustration and are not intended to limit the present invention.

EXAMPLE 1

5g of acetoxymethyl (5R,6S)-2-carbamoyloxymethyl-6-[1-(R)-hydroxyethyl]-penem-3-carboxylate      [(II):

R1=CH$_2$OCONH$_2$; R2=H; R3=H; R4=CH$_3$] were added to 300 ml of phosphate buffer 0.1N (pH=6). The mixture was added with 4 ml (40 mg) of a suspension of esterase from porcine liver (PLE) in 3.2M ammonium sulfate having an activity of 150 U/mg and stirred at 35° C. for 3 hours. The pH was kept at 6.0 by addition of 0.5N NaOH. At the end of the reaction the mixture was analyzed by HPLC (Column: Partisphere C18 Whatman 5 μm (110×4.7 mm). Mobile phase: A: 0.1M Phosphate buffer (pH=2.5); B: Acetonitrile. Gradient: from 0% B to 80% B in 30 min. Flow rate: 1 ml/min. Detector: UV at 210.8 nm).

The analysis showed the presence of 3.55 g (93%) of (5R,6S)-2-carbamoyloxymethyl-6-[1-(R)-hydroxyethyl]-penem-3-carboxylic acid [(I): R1=CH$_2$OCONH$_2$; R2=H].

EXAMPLE 2

The reaction was carried out as described in Example 1, except that the enzyme used was Lipase A6 (Amano) (500 mg), having an activity of 60 U/mg, and the pH was 7.

The mixture was stirred at 25° C. for 16 hours and analyzed as described in Example 1, showing a yield of 58%.

EXAMPLE 3

The reaction was carried out as described in Example 2, except that the pH was 6.

The mixture was stirred at 35° C. for 13 hours and analyzed as described in Example 1, showing a yield of 89%.

EXAMPLE 4

The reaction was carried out as described in Example 1, except that the enzyme used was lipase from wheat germ (Sigma) (500 mg), having an activity of 6.3 U/mg, and the pH was 6.

The mixture was stirred at 35° C. for 18 hours and analyzed as described in Example 1, showing a yield of 70%.

EXAMPLE 5

The reaction was carried out as described in Example 1, except that the enzyme used was Acylase I from porcine kidney (Serva) (500 mg), having an activity of 16 U/mg, and the pH was 6.

The mixture was stirred at 35° C. for 24 hours and analyzed as described in Example 1, showing a yield of 33%.

EXAMPLE 6

The reaction was carried out as described in Example 1, except that the enzyme used was Lipase A6 (Amano) (500 mg), having an activity of 60 U/mg, and the pH was 6.5.

The mixture was stirred at 35° C. for 14 hours and analyzed as described in Example 1, showing a yield of 66%.

EXAMPLE 7

The reaction was carried out as described in Example 1, except that the enzyme used was Lipase A6 (Amano) (500 mg), having an activity of 60 U/mg, and the pH was 7.

The mixture was stirred at 35° C. for 11 hours and analyzed as described in Example 1, showing a yield of 42%.

EXAMPLE 8

The reaction was carried out as described in Example 1, except that the pH was 7.5.

The mixture was stirred at 35° C. for one hour and analyzed as described in Example 1, showing a yield of 90%.

EXAMPLE 9

60 g of Amberlite XAD-7 were added to a solution of 1 g Lipase A6 from *Aspergillus Niger* (Amano) in 250 ml of 0.01N phosphate buffer (pH=7.5).

The resin mixture was gently stirred overnight at room temperature.

Then, the resin was filtered and washed with 250 ml of the same buffer.

The immobilized enzyme resin was added to a suspension of 5 g of acetoxymethyl (5R,6S)-2-carbamoyloxymethyl-6-[1-(R)-hydroxyethyl]-penem-3-carboxylate [(II): R1=CH$_2$OCONH$_2$; R2=H; R3=H; R4=CH$_3$] in 300 ml of 0.1N phosphate buffer (pH=6). The reaction mixture was stirred at 35° C. for 20 hours. The resin containing the enzyme was separated off by filtration in vacuo through a glass filter and washed with 300 ml of phosphate buffer (pH=6).

The filtrate was analyzed as described in Example 1, showing a yield of 55%.

The immobilized enzyme resin was used for three production cycles without appreciable loss of activity.

EXAMPLE 10

60mg (6 ml suspension in 3.2M (NM$_4$)$_2$SO$_4$ solution, 9000 units) of PLE (Sigma) were transferred into a dialysis bag with 10 ml of 1M phosphate buffer (pH=7.5) and left for 48 hours in 1000 ml of that buffer at 4° C. The contents of the dialysis bag was diluted with 20 ml buffer and mixed with 4 g of acrylic beads (Eupergit C, Rohm Pharma, W. Germany). After 24 hours at room temperature the acrylic beads were filtered off, washed once with 250 ml of buffer and added to a suspension of 5 g of acetoxymethyl (5R,6S)-2-carbamoyloxymethyl-6-[1-(R)-hydroxyethyl]-penem-3-carboxylate [(II): R1=CH$_2$OCONH$_2$; R2=H; R3 H; R4=CH$_3$] in 300 ml of 0.1N phosphate buffer (pH=6).

The reaction mixture was stirred at 35° C. for 2 hours. The resin containing the enzyme was separated off by filtration in vacuo through a glass filter and washed with 300 ml of phosphate buffer (pH=6).

The filtrate was analyzed as described in Example 1, showing a yield of 92%.

The immobilized enzyme resin was used for 10 production cycles without appreciable loss of activity.

EXAMPLE 11

5 g of methoxycarbonyloxymethyl (5R,6S)-2-carbamoyloxymethyl-6-[1-(R)-hydroxyethyl]-penem-3-carboxylate [(II): R1=CH$_2$OCONH$_2$; R2=H; R3=H; R4=OCH$_3$] were added to 300 ml of phosphate buffer 0.1N (pH=6). The mixture was added with 4 ml (40 mg) of a suspension of esterase from porcine liver (PLE) in 3.2M ammonium sulfate having an activity of 150 U/mg and stirred at 35° C. for 4 hours.

The pH was kept at 6.0 by addition of 0.5N NaOH. At the end of the reaction the mixture was analyzed as described in Example 1. The analysis showed the presence of 3.4 g (89%) of (5R,6S)-2-carbamoyloxymethyl-6-[1-(R)-hydroxyethyl]-penem-3-carboxylic acid [(I): R1=CH$_2$OCONH$_2$; R2=H].

EXAMPLE 12

The reaction was carried out as described in Example 2, except that the pH was 5.5. The mixture was stirred at 35° C. for 20 hours and analyzed as described in Example 1, showing a yield of 90%.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the U.S. is:

1. An in vitro process for preparing a compound of the formula I:

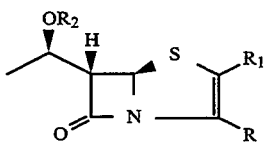

wherein R represents a carboxy group or carboxylate anion:

$R_1$ represents carbamoyloxymethyl or methoxymethyl;

$R_2$ represents a hydrogen atom or a hydroxy-protecting group selected from the group consisting of p-nitrobenzyloxycarbonyl, 2,2,2-trichloroethoxycarbonyl, trimethylsilyl, benzyl, p-bromophenacyl, triphenylmethyl and pyranyl; which process comprises:

a) hydrolyzing a compound of the formula (II):

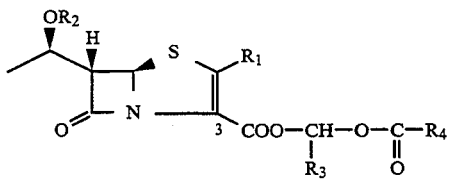

wherein $R_1$ and $R_2$ are as defined above; $R_3$ represents a hydrogen atom; and $R_4$ represents lower alkyl or lower alkoxy; by means of an enzyme capable of selectively hydrolyzing the ester group at the 3-position, said enzyme being selected from the group consisting of porcine liver esterase, Pseudomonas sp. cholesterol esterase, porcine kidney acylase I, *Chromobacterium viscosum* lipase, *Penicillum liliacinum* lipase B, *Rhizopus javanicus* lipase FAP 15, *Aspergillus niger* lipase A 6, wheat germ lipase, *Rhizopus delamar* lipase, Pseudomonas sp., lipase P, porcine kidney lipase SP 225, Pseudomonas sp. lipoprotein lipase, *Candida cylindracea* lipase OF, Pseudomonas sp. lipase CES, *Penicillum cyclopium* lipase 6, *Penicillum roqueforti* lipase R-10, *Candida lipolytica* lipase L-10, *Rhizopus delamar* lipase D-20 and *Candida cylindracea* lipase AY 30; and further wherein said enzymatic hydrolysis is effected at a pH in the range of from 5 to 8 and at a temperature in the range of 20° C. to 40° C., with the proviso that when $R_4$ is lower alkoxy, the enzyme used is porcine liver esterase; and b) recovering said compound of the formula (I).

2. The process of claim 1, wherein $R_2$ is p-nitrobenzyloxycarbonyl, trimethylsilyl or pyranyl, and $R_4$ is methyl.

3. The process of claim 1, wherein $R_4$ is ethyl or ethoxy.

4. The process of claim 1, wherein $R_4$ is methyl.

* * * * *